(12) United States Patent
Campbell Leckey (10) Patent No.: US 10,006,886 B2
(45) Date of Patent: Jun. 26, 2018

(54) ENERGY ANALYSIS METHOD FOR HIDDEN DAMAGE DETECTION

(71) Applicant: The United States of America as represented by the Administrator of the National Aeronautics and Space Administration, Washington, DC (US)

(72) Inventor: Cara A. Campbell Leckey, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 323 days.

(21) Appl. No.: 14/709,887

(22) Filed: May 12, 2015

(65) Prior Publication Data

US 2016/0011151 A1    Jan. 14, 2016

Related U.S. Application Data

(60) Provisional application No. 62/022,310, filed on Jul. 9, 2014.

(51) Int. Cl.
  *G01N 29/04*   (2006.01)
  *G01N 29/24*   (2006.01)
  *G01N 29/44*   (2006.01)

(52) U.S. Cl.
  CPC ....... *G01N 29/043* (2013.01); *G01N 29/2437* (2013.01); *G01N 29/4436* (2013.01); *G01N 2291/0231* (2013.01); *G01N 2291/2694* (2013.01)

(58) Field of Classification Search
  CPC ..... G01N 29/043; G01N 29/2437; G01N 3/08
  See application file for complete search history.

(56) References Cited

U.S. PATENT DOCUMENTS

2012/0035862 A1* 2/2012 Kollgaard ............ G01N 29/043
                                                           702/39

OTHER PUBLICATIONS

Sohn, H. et al., "Delamination Detection in Composites Through Guided Wave Field Image Processing," Composites Science Technology, 2011, pp. 1250-1256, vol. 71.
Tian, Zhenhua et al., "Guided Wave Propagation Study on Laminated Composites by Frequency-Wavenumber Technique," Proceedings of SPIE, Apr. 10, 2014, pp. 1-11, vol. 9063.
(Continued)

*Primary Examiner* — David M Gray
*Assistant Examiner* — Andrew V Do
(74) *Attorney, Agent, or Firm* — Andrea Z. Warmbier; Robin W. Edwards; Mark P. Dvorscak (57) ABSTRACT

A method of detecting internal defects in composites or other multilayer materials includes generating a wavefield on a surface of the material. Wavefield data is collected from the wavefield on the surface, and the measured wavefield data is processed to provide measured energy data. The method may include generating simulated or predicted energy data for the multilayer material that is compared to the simulated energy data to determine if the multilayer material has internal defects or damage below the surface. The method can be utilized to detect and/or quantify damage or other defects that are "hidden" by damage that is closer to the surface of the material.

19 Claims, 7 Drawing Sheets

(56) References Cited

OTHER PUBLICATIONS

Michaels, Jennifer E. et al., "Approaches to Hybrid SHM and NDE of Composite Aerospace Structures," Proceedings of SPIE, Mar. 9, 2014, pp. 1-9, vol. 9064.
Glushkov, E Vgeny et al., "Wave Energy Trapping and Localization in a Plate with a Delamination," Smart Materials and Structures, 2012, pp. 1-12, vol. 21.
Leckey, Cara A.C. et al., "Guided Waves in Anisotropic and Quasi-isotropic Aerospace Composites: Three-dimensional Simulation and Experiment," Ultrasonics, 2014, pp. 385-394, vol. 54.
Marklein, Rene, "The Finite Integration Technique as a General Tool to Compute Acoustic, Electromagnetic, Elastodynamic, and Coupled Wave Fields," Review of Radio Science 1999-2002, pp. 201-244, John Wiley & Sons, New York.
K-cluster NASA LaRC, http://k-info.larc.nasa,gov/, webpage last accessed Apr. 28, 2015.
Pavlakovic, Brian et al., "Disperse: A General Purpose Program for Creating Dispersion Curves," Review of Progress in Quantitative Nondestructive Evaluation, 1997, pp. 185-192, vol. 16A, Plenum Press, New York.

* cited by examiner

ENERGY ANALYSIS METHOD FOR HIDDEN DAMAGE DETECTION

CROSS-REFERENCE TO RELATED PATENT APPLICATION

This patent application claims the benefit of and priority to U.S. Provisional Patent Application No. 62/022,310, filed on Jul. 9, 2014, the contents of which are hereby incorporated by reference in their entirety.

STATEMENT REGARDING FEDERALLY SPONSORED RESEARCH OR DEVELOPMENT

The invention described herein was made by an employee of the United States Government and may be manufactured and used by or for the Government of the United States of America for governmental purposes without the payment of any royalties thereon or therefore.

FIELD OF THE INVENTION

This invention relates to nondestructive evaluation (NDE) of structures, and more particularly to an NDE that measures energy trapping to detect damage that may be present below the surface of multilayered materials.

BACKGROUND OF THE INVENTION

Damage can occur internally to composite aerospace materials, where it is not visible on the surface. Various nondestructive methods have been developed for detecting internal damage. However, prior to the present invention, there was no method for detecting "shadowed" or hidden damage (e.g., damage disposed below/overlapping damage near the surface) with only single sided access to the specimen (which is the case in many real-world settings, such as access to only the exterior of aircraft or space vehicle). The extent of damage (including any shadowed/hidden damage) correlates to how the damage grows in the material. As more aeronautics and space vehicles use more extensive amounts of composite materials, detecting the full extent of damage is increasingly important for composite vehicles/components.

Damage or other defects can exist both close to an accessible (e.g., outer) surface and towards an inaccessible (e.g., inner) surface of a structure. The damage located near the accessible surface can hide (or shadow) damage that exists directly below it when inspected from the accessible side/surface. "Below" as used herein means further from the accessible side or surface (regardless of the orientation of the accessible side/surface), and "directly below" means further from the accessible side or surface and at least partially overlapping (regardless of the orientation of the accessible side/surface). Current NDE techniques which can be deployed in a real-world non-laboratory setting and can be applied to components/structures larger than a coupon size only detect the near surface damage, and cannot detect the hidden damage. Current NDE techniques (such as ultrasonic scans) cannot detect the type of hidden/shadowed damage described above when only single sided access is available. Current NDE techniques can only detect the near surface non-shadowed damage, and therefore do not yield data that can identify or quantify the full damage extent.

Prior studies published in the scientific literature have investigated the phenomenon of guided wave energy trapping in delaminated plate-like components, such as composites. Prior studies reported in the scientific literature have also investigated cumulative energy due to wave trapping. However, these studies only investigated energy trapping in relation to locating damage, and/or sizing the near surface damage. Specifically, these prior studies focused on identifying damage in cases where only a single layer of damage exists. However, this is not a realistic scenario for composites in which damage typically occurs as multiple damage layers at multiple ply levels through the composite thickness. Prior methods cannot identify the presence of hidden "shadowed" damage. Additionally, prior NDE methods are not capable of detecting hidden "shadowed" damage in situations that are limited to single sided access. Current NDE techniques (such as ultrasonic and thermographic methods) for single sided access scenarios are limited to only detecting the near surface (non-hidden) damage.

Accordingly, there is a need for a novel nondestructive method of detecting internal damage in various structures, including aerospace materials.

BRIEF SUMMARY OF THE INVENTION

One aspect of the present invention is a method of detecting internal defects in an item comprising a composite or other multilayer material. The method includes connecting at least one transducer to an item comprising a multilayer material. The transducer is actuated to generate an ultrasonic guided wavefield in the material, including on a surface of the item, such that energy is trapped near the surface of the item above any existing damage (between any existing damage and the surface of the item). Ultrasonic guided wavefield data is then collected from the wavefield on the surface of the item, and the guided wavefield data is processed to provide measured energy data. The method further includes generating simulated energy data for the multilayer material. The measured energy data is compared to the simulated energy data for the multilayer material to determine if the multilayer material has internal defects or damage below the surface of the item. The transducer may comprise a piezoelectric transducer, and a laser doppler vibrometer (LDV) may be utilized to collect guided wavefield data from the surface of the item. The measured energy data may comprise cumulative measured energy data, and the simulated energy data may comprise cumulative simulated energy data that is generated utilizing a computer simulation or other suitable numerical process.

Another aspect of the present invention is a method of detecting internal defects in a multilayer material. The method includes applying a force to the multilayer material, and measuring a response of the surface to the applied force to thereby provide measured surface response data. The measured surface response data is compared to known data that correlates surface responses for the multilayer material to internal defects in the material. The known data includes at least one outer internal defect and at least one internal defect that is disposed a greater distance from the surface than the outer internal defect. The outer internal defect and the inner internal defect at least partially overlie one another such that the inner internal defect is at least partially hidden by the outer internal defect. The method further includes determining if at least one hidden internal defect is present by comparing the measured surface response data to the known data. The known data may comprise surface response data for internal damage. The known data may also comprise simulated surface response data, or the known data may comprise empirical data for the multilayer material. Measuring the response of the surface may include measuring at least one of a surface displacement or a surface velocity. Measuring the response of the surface may comprise measuring wavefield data. The known data may comprise simulated cumulative energy data, and the method may include processing the wavefield data to provide measured cumulative energy data. The method may include comparing the measured cumulative energy data to the simulated cumulative energy data to determine if a hidden internal defect is present and/or to quantify a hidden internal defect. The method may include comparing the measured cumulative energy data to the empirical measurements of cumulative energy for the material to determine if a hidden internal defect is present and/or to quantify a hidden internal defect. The force may be applied to the surface in a direction that is transverse or in-plane to the surface.

These and other features, advantages, and objects of the present invention will be further understood and appreciated by those skilled in the art by reference to the following specification, claims, and appended drawings.

DETAILED DESCRIPTION OF THE INVENTION

Figure 1A:
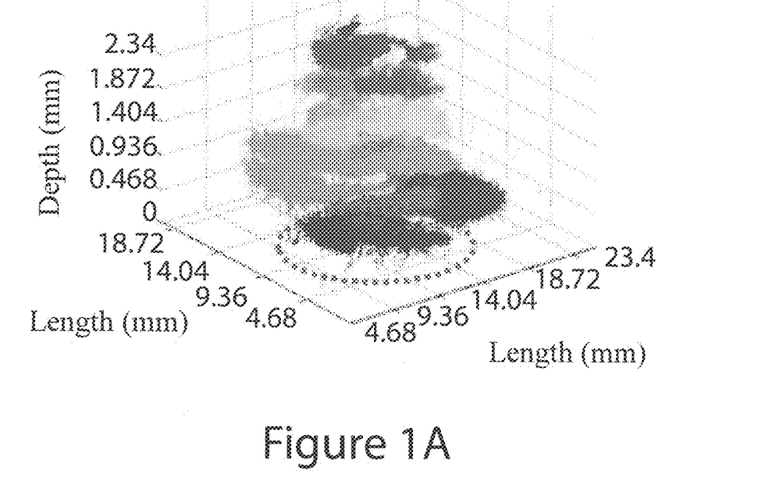
FIG. 1A is a 3D damage map created from microfocus X-ray computed tomography scans showing internal delamination damage in a CFRP coupon plate.
Figure 3A:
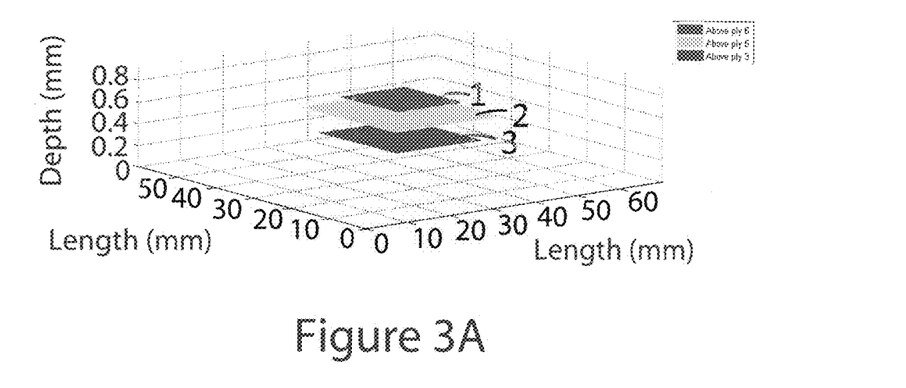
FIG. 3A is a schematic isometric representation of simulated delamination.

For purposes of description herein, the terms "upper," "lower," "right," "left," "rear," "front," "vertical," "horizontal," and derivatives thereof shall relate to the invention as oriented in FIGS. 1A and 3A. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention includes a novel method for identifying the presence of hidden damage in aerospace materials (e.g., hidden delamination damage) using trapped energy analysis. The method may be utilized to detect the presence of hidden damage in multilayered materials such as aerospace composites. The present invention also has the benefit of detecting hidden damage when only single sided access is available (as in most real-world scenarios where access is only available to the outside of an aircraft or spacecraft component). The method includes exciting ultrasonic guided waves in the material (component/specimen/vehicle) using one or more piezoelectric transducers that are permanently attached in-situ or temporarily attached. It will be understood that "hidden" damage or defects as used herein generally refers to delaminations or the like that are further from an accessible surface than delaminations or the like that are directly between (overlapping) the hidden damage or defects and the surface. This type of damage may be referred to as "hidden" damage because it cannot be detected utilizing prior NDE techniques if only one surface of a component is accessible. However, this type of "hidden" damage can be detected utilizing the present invention, and this type of damage is therefore not "hidden" in an absolute sense.

Figure 1B:
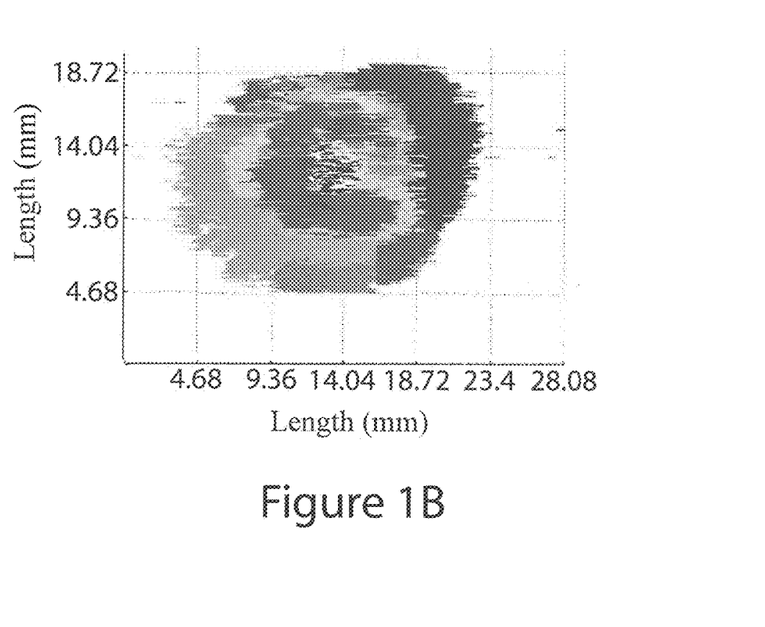
FIG. 1B is a top plan view of the damage map of FIG. 1A.

In a single sided access scenario, the full extent of multilayer (multiple ply) delamination damage can be hidden beneath near surface delaminations that mask/conceal lower damage, as shown in FIGS. 1A and 1B. FIGS. 1A and 1B show delamination damage occurring internally in a quasi-isotropic 26 ply thick carbon-fiber-reinforced polymer (CFRP) plate, created by an impact (quasi-static indentation). FIG. 1A shows the 3D damage map created from microfocus X-ray computed tomography scans of a small coupon sized CFRP plate taken at 23.4 micron resolution taken in a laboratory setting. In FIG. 1A, the impact surface corresponds to a depth of z=3.22 mm (top of the figure). In FIG. 1A, the region circled by the dashed line is an example of damage that would be hidden by upper delamination damage during a single sided NDE scan (assuming access to the impacted surface). FIG. 1B shows the damage map as viewed from the impact side, demonstrating that the extent of lower ply delamination damage is hidden by upper delaminations.

The method may also include measuring and recording guided wavefield data on the surface of a specimen/material using a noncontact laser doppler vibrometer (LDV) or other suitable device such as air-coupled ultrasound. The LDV may have a single laser that measures surface displacement (movement) at a single point, or the LDV may comprise a plurality of laser beams that simultaneously measure surface displacements at a plurality of points corresponding to each laser beam. The present method includes a process to interpret the resulting wavefield data to yield data that can be utilized to determine if hidden shadowed damage is present, and to quantify the hidden damage. The cumulative energy is calculated from the wave field data for the accessible surface of the material/component/vehicle. Due to the physics of guided wave interaction with damage, including multi-layer damage, the energy trapped near the accessible surface varies depending on whether there is hidden shadowed damage present, and varies depending on the extent of that hidden damage.

The method also includes using validated ultrasonic guided wavefield computer/mathematical simulations to determine how much expected trapped energy there will be for different damage scenarios. Specifically, experimental (i.e. measured) data may be compared to simulation cases with and without hidden damage for numerous simulated damage scenarios (such as a single hidden damage, or multiple hidden damages) and including various geometries of damage. Experimental (i.e., measured) data may be used to guide a down-select of simulated cases based on the size of detected non hidden near surface damage. The processed (measured) wavefield data (which has been processed to yield cumulative energy data) is correlated to the simulation cumulative energy analysis result. The presence of hidden damage in the experimental (test) case is identified (and optionally quantified) via these comparisons. Thus, measured test data taken from test samples having known damage can be compared to the computer simulations to verify that the simulations accurately predict the cumulative energies corresponding to specific damage.

In another embodiment, functional operation would entail the steps described above being applied to a real-world aerospace component/vehicle/specimen: 1) Guided waves are excited in the material using a piezoelectric transducer or by laser excitation/generation of guided waves. 2) Wavefield data is collected for the accessible specimen surface using a LDV to scan the specimen surface (or, optionally an airborne ultrasound to collect wavefield data). If an LDV having a single laser is used, the piezoelectric or laser generation is re triggered at each position of the LDV such that data of wavefield versus position is collected for a specified length of time. If an LDV having a plurality of lasers is utilized, the LDV may only need to be positioned once, and a single actuation of the piezoelectric may be sufficient. 3) The measured wavefield data is processed to yield the cumulative energy. 4) The measured cumulative energy is compared to cumulative energy from simulated cases with and without hidden damage or defects (for numerous damage defect scenarios). 5) Via this comparison the presence of hidden damage or other defects is identified. The hidden damage may also optionally be quantified. Specifically, a specific trend in cumulative energy as multiple damage layers were added has been shown in testing, and these trends may be utilized to quantify the damage.

As discussed above, simulations for various damage scenarios can be validated by comparing the simulations to specimens having no damage and specimens having known damage. In general, a specimen may comprise a relatively small piece of material (e.g., a composite plate) that can be assessed from all sides and analyzed utilizing X-rays or other techniques to determine the extent of the damage, even if the damage comprises multiple layers that would be hidden in a one-sided access scenario (e.g., an aircraft structure). The validated computer simulations can be utilized to determine the predicted wavefield data and cumulative energy for various damage scenarios in materials having a wide range of configurations (e.g., fiber orientations, number of plies, etc.). The ability to provide "known" cumulative energy data by accurately predicting the expected cumulative energy utilizing wavefield simulations eliminates the need to empirically test the effect of damage on the cumulative energy in all material compositions, fiber orientations, etc. to be inspected.

However, it will be understood that simulations are not necessarily required to detect and/or quantify hidden damage in single sided access situations. For example, if an airplane wing has a known composite layup/structure, a plurality of specimens (e.g., plates) having an identical layup can be fabricated. The specimens may be damaged to varying degrees (e.g., impacted utilizing objects having different known masses at different known velocities), and the damage in the specimens may be determined utilizing X-ray measurement or other techniques that cannot be utilized in the aircraft wing itself due to the one-sided access. Specimens can also be fabricated with known inserted damage (e.g., Teflon inserts). A piezoelectric device can then be utilized to excite guided wavefields on the surfaces of the damaged specimens, and an LDV can be utilized to collect wavefield data for each specimen/type of damage. This data can be processed to provide known cumulative energy data. A piezoelectric device can then be positioned on the aircraft wing or other aircraft component/structure such as fuselage, and an LDV can be utilized to measure the response of the component/structure due to the actuation of piezoelectric device. The measured wavefield data can then be processed to yield measured cumulative energy data, and the measured cumulative energy data can be compared to the known cumulative energy data for the test samples to determine if damage in the component is present and/or to quantify the extent of the damage.

As discussed above, one aspect of the present invention is a method or process for detecting damage in composites or other layered materials. However, the present energy analysis method may also be utilized to detect and/or quantify imperfections or defects that are not a result of damage. For example, during fabrication of a composite structure defects such as delaminations may be present in the composite structure due to variations in the fabrication process. The methods described above for detecting damage in layered or composite materials may also be utilized to detect imperfections/defects that occur during fabrication of a structure. Furthermore, it will be understood that the present invention may detect other types of damage or imperfections resulting from, for example, overloading of a composite structure, fatigue, stresses resulting from changes in temperature, or other environmental conditions. Thus, the present invention may be utilized to detect numerous types of defects in materials in addition to defects resulting from damage to a structure.

Also, as discussed above, a single piezoelectric transducer may be connected to the surface of an item to be inspected and actuated while an LDV is used to measure the surface movement/response. If a relatively large area is to be inspected, the piezoelectric transducer can be detached and moved to a new location, actuated, and a LDV may be utilized to measure the wavefield data at the surface resulting from the piezoelectric transducer. Alternatively, a plurality of piezoelectric transducers can be positioned on a surface to be inspected at spaced apart locations. The piezoelectric transducers can then be actuated simultaneously or sequentially, and the resulting movement of the surface can be measured utilizing an LDV. An LDV having a single laser may be utilized by moving the laser to different points on the surface prior to actuation of the piezoelectric transducers. Alternatively, an LDV having a plurality of laser beams capable of simultaneously measuring the surface response at a plurality of locations may be utilized to simultaneously measure the surface response at a plurality of locations. In this way, an aircraft structure or the like having a relatively large surface area can be inspected without moving the LDV. It will be understood that very large surface areas may require movement of a multiple laser LDV in order to measure the surface response over a large area.

Also, it will be understood that the present invention is not necessarily limited to use of piezoelectric transducers. In general, virtually any suitable device or technique that generates a force on the structure can be utilized. For example, other types of laser, electrical or hydraulic devices capable of generating a force on the structure to be tested may be utilized.

Furthermore, it will be understood that the piezoelectric transducers or other force-generating devices may be attached to a surface of a structure to be inspected, or the piezoelectric transducers may be integrally formed with the structure at the time the structure is fabricated. For example, piezoelectric transducers may be imbedded in composite materials prior to curing. The piezoelectric transducers or other force-generating devices may then be actuated at a later time to inspect the structure. For example, an aircraft fuselage or wing structure may be fabricated from a composite material, and piezoelectric transducers may be disposed in the laminate prior to curing. Electrical lines or other utility lines may also be disposed in the structure during fabrication. During subsequent inspection of the aircraft, the piezoelectric transducers can be actuated utilizing the lines imbedded in the structure, and an LDV or other suitable device can be utilized to measure the response of the surface. This response can then be compared to simulations for the aircraft structure, or to empirically-generated data to detect damage or other defects in the composite material.

The present invention may be used for any multi-layered material, not just composites. Additionally, wavefield data could be collected via other means such as airborne scanning ultrasound. As discussed below, experimental testing has demonstrated that energy trapped at the surface increased as the number of delaminations through the thickness increased (i.e. as the number of hidden delaminations has increased).

Elastodynamic Finite Integration Technique Simulations

Elastodynamic finite integration technique (EFIT) was implemented for the simulation examples discussed below. Validation of the custom code via comparisons to experiment and theory are reported in C. A. C. Leckey, M. D. Rogge, F. R. Parker, "Guided waves in anisotropic and quasi-isotropic aerospace composites: Three-dimensional simulation and experiment," Ultrasonics 54 (2014) 385-394, the entire contents of which are incorporated herein by reference. An overview of finite integration technique can be found in R. Marklein "The finite integration technique as a general tool to compute acoustic, electromagnetic, elastodynamic, and coupled wave fields," in: ("Rev. Radio Sci.: 1999-2002 URSI, IEEE Press and John Wiley and Sons, New York, (2002), pp. 201-244,") the entire contents of which are incorporated herein by reference. The code is parallelized to run efficiently on cluster computing and many-core resources and the simulations implemented for this paper were run on NASA Langley's k2-cluster ("K-cluster NASA LaRC, http://k-info.larc.nasa.gov/,") the entire contents of which are incorporated herein by reference. Ply level material properties were incorporated into the EFIT simulations, with the stiffness matrix rotated according to the ply layup. The custom 3D EFIT code calculates stress and velocity at all points in the simulated composite. Simulation output of the in-plane and out-of-plane velocities (i.e., wavefield) at the composite surface is analogous to correspond to the type of wavefield data that can be recorded experimentally using a 3D scanning laser Doppler vibrometer (SLDV).

Multilayer Delamination Studies

Figure 2A:
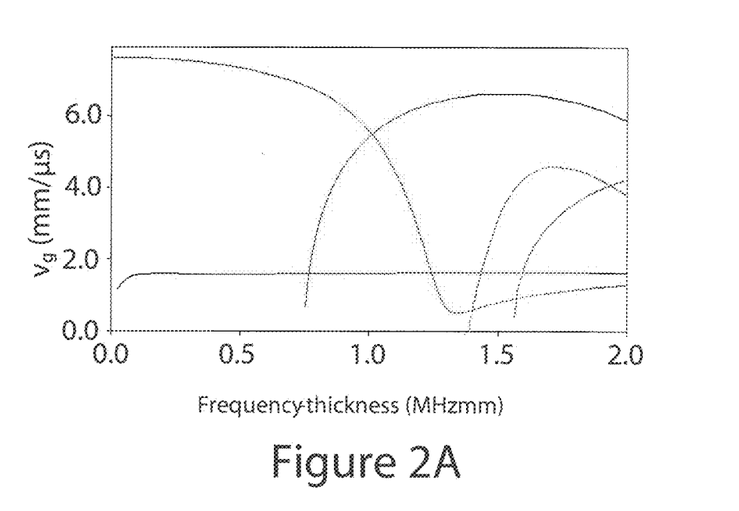
FIG. 2A is a graph showing group velocity ($V_g$) dispersion of a composite material.
Figure 2B:
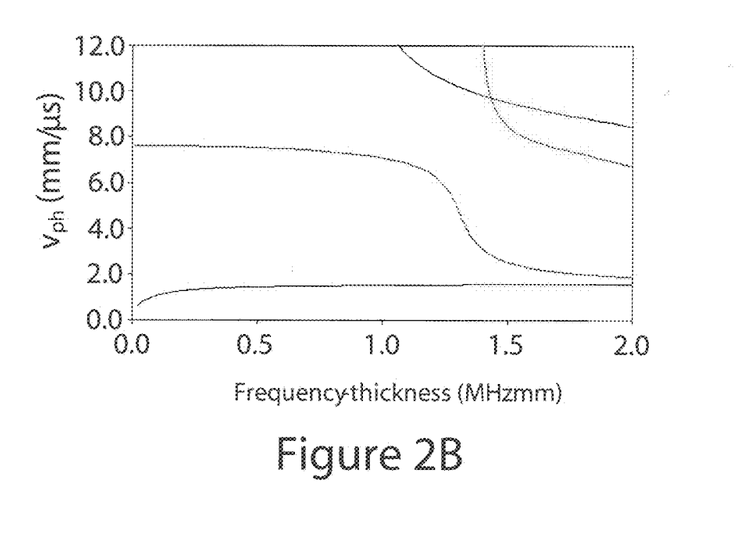
FIG. 2B is a graph showing phase velocity ($V_{ph}$) dispersion of a composite material.

The simulations reported herein are for an 8-ply IM7/8552 CFRP composite plate with layup $[(0/90)_2]_s$. A small spatial step size of 19 microns was used in order to accurately capture the wave behavior in the thin material regions above/between/below delaminations. The size of the simulated plate is 60 mm×70 mm×0.92 mm. In all simulation cases a 300 kHz 3-cycle Hann windowed sine wave was excited over a 12.6 mm diameter circular region (representing a circulate piezoelectric transducer). At this frequency-thickness (0.28 MHz-mm) two guided wave modes exist, as shown in the corresponding dispersion curves in FIGS. 2A and 2B. FIGS. 2A and 2B show group and phase velocity dispersion curves, respectively, along the 0 degree direction for an 8-ply IM7/8552 CFRP plate of layup [(0/90)2]s, calculated using DISPERSE software. The lines are symmetric modes and the blue lines are antisymmetric modes. Delaminations were simulated by implementing stress-free boundary conditions at damage locations.

Figure 3B:
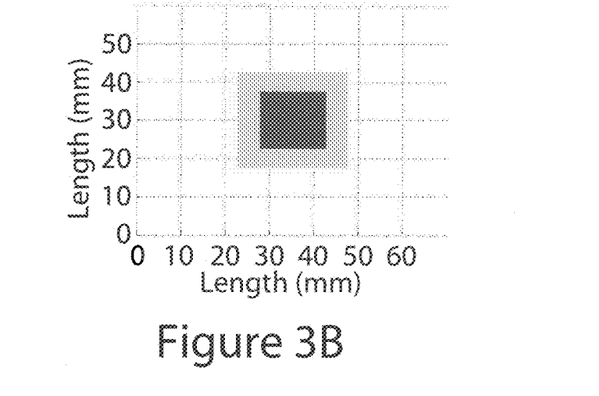
FIG. 3B is a top plan view of the simulated delamination of FIG. 3A.

Four cases (FIGS. 3A and 3B) were simulated to study the changes in energy napping due to multilayer delamination damage in CFRP composites. The four cases are as follows: Case 0—pristine case (i.e., no damage); Case 1—a single 15 $mm^2$ delamination located "above" (i.e., closer to the surface) the $6^{th}$ ply; Case 2—the 15 $mm^2$ delamination from case 2 plus an additional 25 $mm^2$ delamination located above the $5^{th}$ ply; Case 3—the delaminations from cases 2 and 3 plus an additional 20 $mm^2$ delamination located above the $3^{rd}$ ply. The three damage cases are shown in FIGS. 3A and 3B. In Case 3 the lower 20 $mm^2$ delamination is hidden by the upper two delaminations if only single sided inspection access is available (i.e., traditional NDE techniques such as ultrasonic C-scan would not detect the presence of the $3^{rd}$ delamination).

FIGS. 3A and 3B represent simulated delamination cases: 1) single 15 $mm^2$ delamination 1 located above ply 6, 2) delamination from case 1 plus a 25 $mm^2$ delamination 2 located above the $5^{th}$ ply, 3) delaminations from Cases 1 and 2 plus a third 20 $mm^2$ delamination 3 located above the 3rd ply. FIG. 3A is a volumetric (schematic) view of the delamination locations, and FIG. 3B shows a top view of the delaminations (viewed from the 'top' of the composite plate which represents the accessible side). In Case 3 the lower delamination 3 is hidden by the upper two delaminations due to the overlap of the upper two delaminations. In FIGS. 3A and 3B, the outer (accessible) surface faces upwardly. Thus it will be understood that the terms "upper" and "lower" refer to the simulated material when orientated as shown in FIGS. 3A and 3B. In this context, "upper" generally means closer to the outer accessible surface of the material, and "lower" generally means further from the outer accessible surface.

Figure 4:
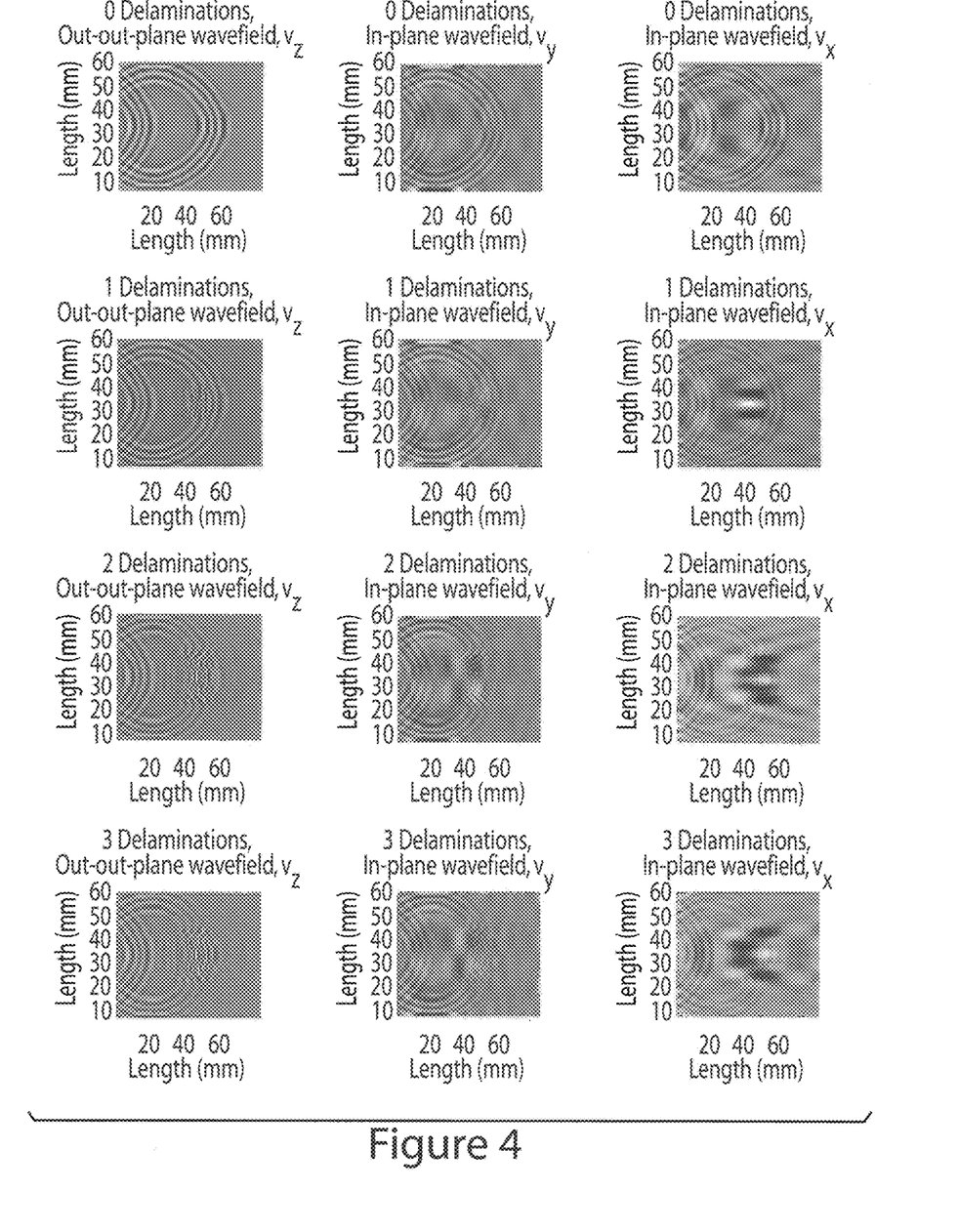
FIG. 4 is a single snap shot in time of out-of-plane wavefields $V_z$, in-plane wavefield $V_y$, ($2^{nd}$ column), and in-plane wavefield $V_x$ (3rd column) at a composite surface for two simulated cases, namely, 0 delaminations (top row), 1 delaminations ($2^{nd}$ row), 2 delaminations ($3^{rd}$ row), and 3 delaminations ($4^{th}$ row)

FIG. 4 shows a single snapshot in time of the in-plane and out-of-plane wavefields $V_z$ (first column) and in-plane wavefields $V_y$ and $V_x$ ($2^{nd}$ and $3^{rd}$ columns, respectively) at the composite surface for the four simulation cases discussed above in connection with FIGS. 3A and 3B. Thus, the simulated wavefields at the surface are affected by the simulated delaminations: specifically, the top row=Case 0 (pristine case), the 2nd row=Case 1 (single delamination), the 3rd row=Case 2 (two delaminations), the 4th row=Case 3 (three delaminations). In the images for the delaminated cases i.e., rows 2-4) energy trapping is clearly visible as remaining wave energy above the delaminated regions after the incident waves have passed by. At the point in time shown in the images, the slower asymmetric mode can be observed as it passes beyond the damage region. Thus, the simulated wavelengths at the surface are affected by the simulated delaminations.

Figure 5A:
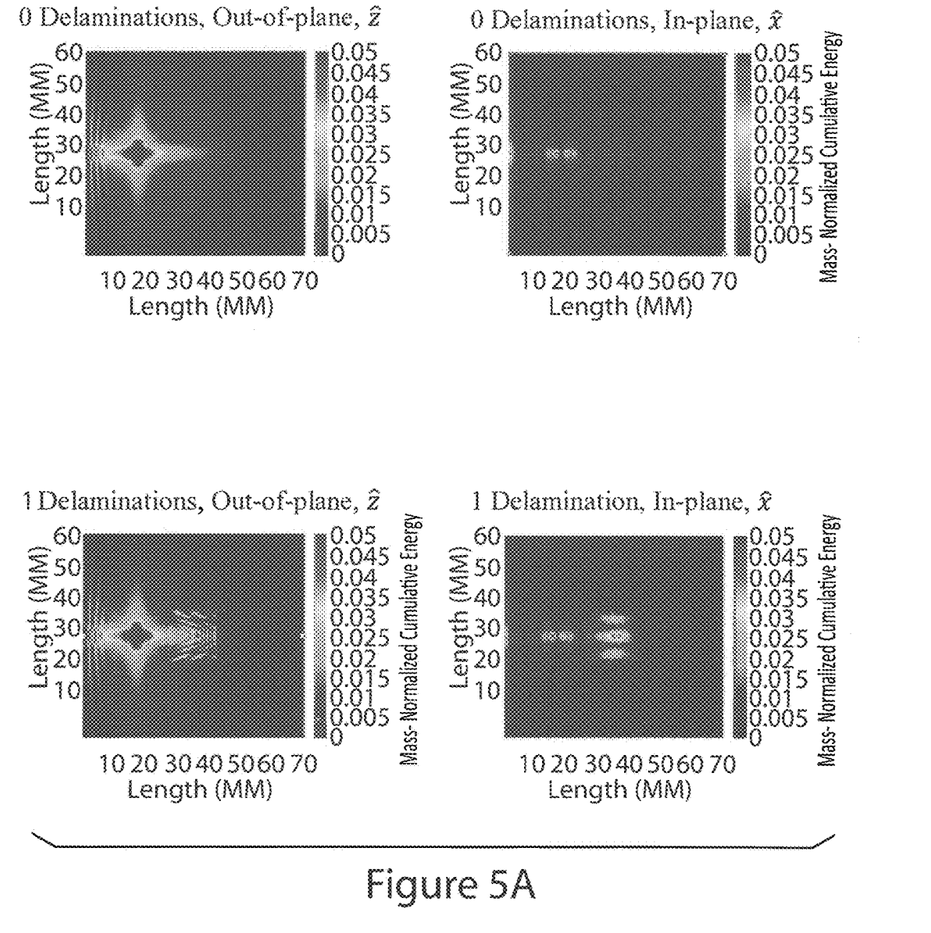
FIG. 5A shows out-of-plane ($1^{st}$ column), and in-plane ($2^{nd}$ column) mass-normalized cumulative energy at the composite surface for two simulated cases, namely 0 delaminations and 1 delaminations.
Figure 5B:
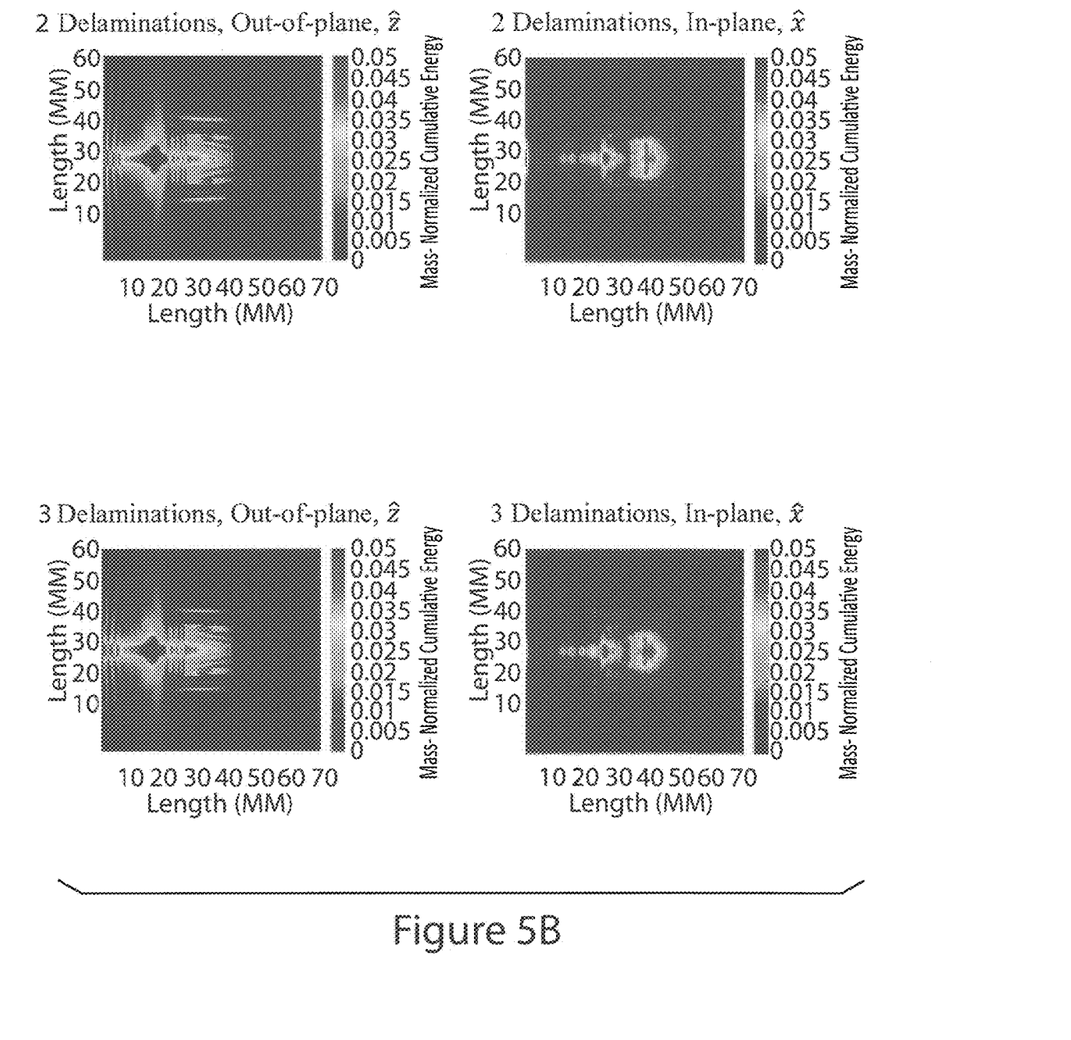
FIG. 5B shows out-of-plane ($1^{st}$ column) and in-plane ($2^{nd}$ column), mass-normalized cumulative energy at the composite surface for two simulated cases, namely 2 delaminations ($1^{st}$ row) and 3 delaminations ($2^{nd}$ row)

Following the notation used by Sohn et al. ("Delamination detection in composites through guided wave field image processing," Compos. Sci. Technol., (2011) pp. 1250-1256 the entire contents of which are incorporated herein by reference), the mass-normalized cumulative energy can be calculated for the surface of the composite:

$$E_i(x,y,z,t) = \int_{t_1}^{t_2} \frac{1}{2} v_i^2 dt \qquad (1)$$

where $E_i$ is the mass-normalized cumulative energy of component i, vi is the i velocity component, and the integral is taken over a time span from time $t_1$ to time $t_2$. In practice for the discrete time wavefield, a summation is taken in place of the integral. FIG. 5 shows the mass-normalized cumulative energy at the top surface of the composite sample for $E_z$ and $E_x$ components of the simulated cases. $E_y$ is not shown in order to show larger sized $E_z$ and $E_x$ plots. The high cumulative energy region located near x=18, y=30 is the location of the excitation. The simulated excitation was introduced normal to the composite surface, and hence is larger in the out-of-plane result. However, it will be understood that in-plane excitation may also be introduced in simulations and in actual inspection and/or validation.

Figure 6A:
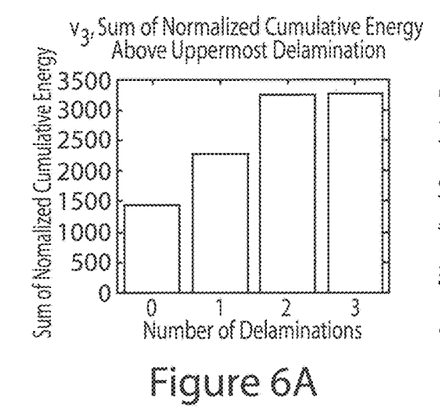
FIG. 6A is a chart showing the sum of the cumulative energy for out-of-plane movement at a $V_3$ composite surface above the uppermost delamination for the four simulated cases of FIG. 4.
Figure 6B:
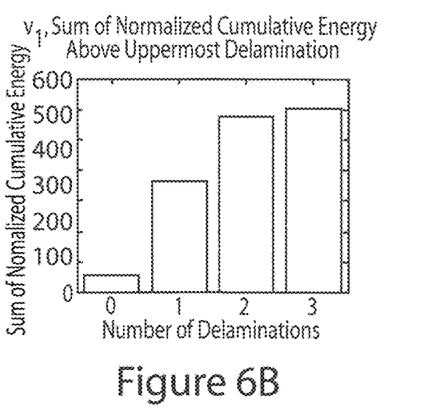
FIG. 6B is a chart showing the sum of cumulative energy for in-plane movement $V_1$ at a composite surface above the upper most delamination for the four simulated cases.
Figure 6C:
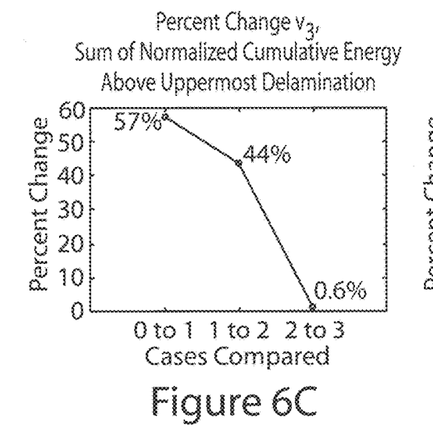
FIG. 6C is a graph showing the percent change in the summed cumulative out-of-plane energy for out-of-plane movement $V_3$ for the four simulated cases.
Figure 6D:
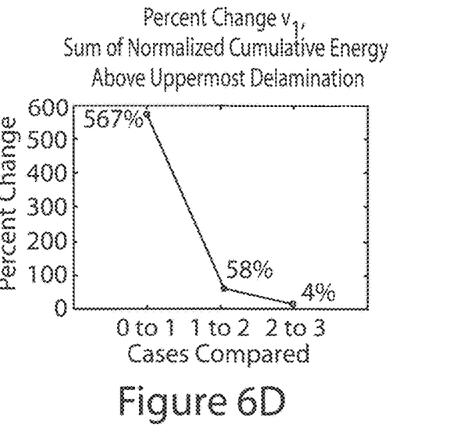
FIG. 6D is a graph showing the percent change in the summed cumulative in-plane energy for the in-plane movement $V_1$ for the four simulated cases.

In FIGS. 5A and 5B, the left and right columns shows out-of-plane and in-plane mass-normalized cumulative energy at the composite surface respectively, for the four simulated cases discussed above in connection with FIGS. 3A and 3B specifically, in FIG. 5A the top row=Case 0 (pristine case), and the 2nd row=Case 1 (single delamination). In FIG. 5B, the top row=Case 2 (two delaminations), and the $2^{nd}$ row row=Case 3 (three delaminations). The dashed white lines forming boxes in FIGS. 5A and 5B designate the perimeter of the delaminations as visible from the top view. Since the plots show the cumulative energy on the top composite surface (i.e., the energy as viewed from "above"), only the upper two delamination perimeters are shown. The third delamination is hidden entirely below the upper two. Trapped energy in the delaminated regions is clearly visible in the images in Figures SA and SB. In fact, the size and shape of the uppermost delamination is distinguishable in the out-of-plane cumulative energy plots. In Cases 2 and 3, additional trapped energy above the largest (25 mm$^2$) delamination is observed in the regions that extend beyond the uppermost (15 mm$^2$) delamination. Since the perimeter of the upper delamination is distinguishable in the wavefield and energy plots, the next step for comparing the three damage cases is to sum the energy at the surface over the uppermost delamination. This summation permits a direct quantitative comparison of the trapped energy over the area at the composite surface corresponding to the damage region of the four simulated cases, as shown in FIGS. 6A, 6B, 6C, and 6D. The results in FIGS. 6A-6D show that trapped energy increases in the damaged region as the number of delaminations through the composite thickness increases. In relation to the detection of hidden delamination damage, there is a small increase in trapped energy from Cases 2 to Case 3 (i.e., slightly more energy is trapped at the surface when the hidden delamination is present). FIGS. 6A and 6B show the sum of the normalized cumulative energy at the composite surface in the region above the uppermost delamination for the out-of-plane energy and in-plane energy $V_1$, respectively. The energy in the pristine case (0 delaminations) is shown along with Cases 1-3 (as noted by axis labels). FIGS. 6C and 6D show the percent change in the summed normalized cumulative out-of-plane (FIG. 6B) and in-plane (FIG. 6D) energy from Cases 0 to 1, Cases 1 to 2 and Cases 2 to 3.

These results demonstrate that analysis of trapped energy above delaminations may be utilized to identify the presence of hidden delamination damage. In practice, the measured trapped energy at the surface of a real composite component I (e.g., aircraft wing or fuselage spacecraft structure, etc.) compared to either an established trend in energy change due to multilayer delamination damage for the specific of-interest composite material and layup, or a library (database) of simulated damage (and corresponding energy) scenarios. Additional simulations including a larger number of delamination scenarios and more realistic delamination geometries (such as that shown in FIG. 1) may be utilized to develop a database of simulated surface response data for large numbers of damage/defect scenarios, and the (known) simulated surface response to data can be compared to measured surface response gathered utilizing a piezoelectric transducer and LDV. This comparison permits detection and/or quantification of hidden damage/defects. Additional testing utilizing material specimens (e.g., composite plates) having damage detected/quantified by X-ray measurement may also be utilized to establish the experimentally measurable sensitivity to changes in trapped energy by means of piezoelectric transducers/LDV.

The simulation results show changes in the trapped energy (in the cases presented, increases in energy) at the composite surface when additional delaminations exist through the composite thickness. Thus, trapped energy measurements may be utilized to identify the presence of hidden delaminations when only single sided access is available to a component/vehicle. No other single sided field-applicable NDE techniques are believed to exist for identifying the type of hidden delamination damage described above.

The invention claimed is:
1. A method of detecting hidden internal defects in a component comprising a multi layer material from a single side of a surface of the component, the method comprising:
   connecting at least one transducer to the component;
   actuating the transducer to generate an ultrasonic guided wavefield in the multilayer material and on the surface of the multilayer material such that guided wave energy is trapped near the surface due to a first defect below the surface;
   collecting wavefield data from the ultrasonic guided wavefield on the surface of the multi layer material at the single side, without contacting the multilayer material, using a non-contact laser Doppler vibrometer or an air-coupled ultrasound device;
   processing the wavefield data, including calculating a cumulative amount of the guided wave energy trapped near the surface using the collected wavefield data; and
   identifying and/or quantifying whether the multilayer material has hidden internal defects that are further from the surface than the first defect and overlap the first defect, including comparing the calculated cumulative guided wave energy to the known cumulative energy data for a sample set of the multilayer materials having known hidden internal defects.
2. The method of claim 1, wherein:
   the component comprises a multilayer composite material having a matrix material and a plurality of layers of fibers.

3. The method of claim 2, wherein:
the matrix comprises a polymer material, and the layers of fibers comprise carbon fibers.

4. The method of claim 3, wherein connecting at least one transducer to a component includes imbedding a plurality of piezoelectric transducers in the multi layer composite material prior to curing the multi layer composite material, and wherein actuating the transducer includes actuating the plurality of piezoelectric transducers after curing the multilayer composite material.

5. The method of claim 1, wherein:
the hidden internal defects comprise damage in the form of at least one hidden delamination.

6. The method of claim 5, wherein:
the damage comprises a first delamination and a second delamination that is spaced apart from the first delamination and at least partially overlaps the first delamination, and wherein the second delamination is directly between the surface of the component and the first delamination.

7. The method of claim 6, wherein:
the damage further comprises a third delamination, and wherein the first and second delaminations are spared apart from the third delamination, and wherein the first and second delaminations are between the third delamination and the surface of the item and wherein the third delamination at least partially overlaps the first and second delaminations.

8. The method of claim 1, wherein:
the component comprises an aircraft structure.

9. The method of claim 1, wherein:
the known cumulative guided wave energy data comprises simulated cumulative guided wave energy data.

10. The method of claim 1, wherein:
the known cumulative guided wave energy data comprises empirical energy data collected from multilayer material samples having hidden internal damage.

11. The method of claim 1, wherein collecting wavefield data from the ultrasonic guided wavefield includes using a plurality of laser beams to scan the surface from the single side.

12. A method of detecting internal defects in a multilayer material having a surface from a single side of the surface, the method comprising:
applying a force to the multilayer material using a piezoelectric transducer such that an ultrasonic guided wave is excited in the multilayer material and on the surface of the multilayer material, and such that guided wave energy is trapped near the surface due to at least one hidden internal defect below the surface;
measuring, from the single side using a laser Doppler vibrometer or an air-coupled ultrasound device that does not contact the multilayer material, a response of the surface to the applied force to provide measured surface response data, including calculating a cumulative amount of the guided wave energy trapped near the surface using the collected wavefield data;
comparing the measured surface response data to known data that correlates surface responses for the multilayer material to internal defects in the material, the known data corresponding to at least one outer internal defect and the at least one hidden internal defect that is disposed a greater distance from the surface than the outer internal defect, and wherein the outer internal defect and the at least one hidden internal defect at least partially overlie one another; and
determining if the at least one hidden internal defect is present and/or quantifying at least one hidden internal defect by comparing the measured surface response data to the known data.

13. The method of claim 12, wherein:
the known data comprises surface response data for internal damage.

14. The method of claim 13, wherein:
the known data comprises simulated surface response data.

15. The method of claim 13, wherein:
the known data comprises empirical data for the multilayer material that is generated by measuring the surface response of samples having internal damage including at least one hidden internal defect.

16. The method claim 12, wherein applying the force to the multilayer material includes:
exciting the piezoelectric transducer using a windowed sine wave.

17. The method of claim 12, wherein:
measuring the response of the surface further includes measuring at least one of a displacement and a velocity of the surface.

18. The method of claim 12, wherein:
the known data comprises simulated cumulative guided wave energy data; and
comparing the measured cumulative guided wave energy data to the simulated cumulative energy data to determine if the hidden internal defect is present and/or to quantify the hidden internal defect.

19. The method of claim 12, wherein:
the force is applied to the surface in a direction that is transverse to the surface.

* * * * *